(12) United States Patent
Ringemann

(10) Patent No.: US 11,096,611 B2
(45) Date of Patent: Aug. 24, 2021

(54) METHOD FOR PROVIDING A SIGNAL QUALITY DEGREE ASSOCIATED WITH AN ANALYTE VALUE MEASURED IN A CONTINUOUS MONITORING SYSTEM

(71) Applicant: Roche Diabetes Care, Inc., Indianapolis, IN (US)

(72) Inventor: Christian Ringemann, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 16/856,180

(22) Filed: Apr. 23, 2020

(65) Prior Publication Data

US 2020/0245916 A1 Aug. 6, 2020

Related U.S. Application Data

(63) Continuation of application No. 16/229,322, filed on Dec. 21, 2018, now Pat. No. 10,667,734, which is a
(Continued)

(30) Foreign Application Priority Data

Jun. 29, 2016 (EP) .................................. 16 176 940

(51) Int. Cl.
*A61B 5/1486* (2006.01)
*A61B 5/145* (2006.01)
(Continued)

(52) U.S. Cl.
CPC ........ *A61B 5/14865* (2013.01); *A61B 5/1495* (2013.01); *A61B 5/14532* (2013.01);
(Continued)

(58) Field of Classification Search
CPC ............ A61B 5/14546; A61B 5/14865; A61B 5/1495; A61B 5/7221; A61B 5/14532; A61B 5/1451; G01N 27/3271
See application file for complete search history.

(56) References Cited

U.S. PATENT DOCUMENTS 5,413,690 A 5/1995 Kost et al.
5,762,770 A 6/1998 Pritchard et al.
(Continued)

FOREIGN PATENT DOCUMENTS

CN 102293637 A 12/2011
CN 102740770 A 10/2012
(Continued)

OTHER PUBLICATIONS

International Search Report and Written Opinion of the International Searching Authority, PCT/EP2017/065942, dated Sep. 22, 2017, 9 pages.
(Continued)

*Primary Examiner* — Hongmin Fan
(74) *Attorney, Agent, or Firm* — Bose McKinney & Evans LLP

(57) ABSTRACT

A method providing a signal quality degree associated with an analyte value measured in a continuous monitoring system is disclosed. The method includes: receiving a measured analyte value from a biosensor; determining at least two impact parameters, wherein each of the impact parameters is influenced by an operational status of the continuous monitoring system and wherein each of the impact parameters is capable of exerting an influence on the signal quality of the biosensor and wherein the influence of each of the impact parameters on the signal quality of the biosensor is expressed by a weight assigned to each of the impact parameters; and determining the signal quality degree associated with the measured analyte value as a function of the
(Continued)

weights and the corresponding impact parameters; and providing the signal quality degree associated with the analyte value. A method of calibration using the signal quality degree is also disclosed.

17 Claims, 2 Drawing Sheets

Related U.S. Application Data continuation of application No. PCT/EP2017/065942, filed on Jun. 28, 2017.

(51) Int. Cl.
*A61B 5/00* (2006.01)
*A61B 5/1495* (2006.01)
*G01N 27/327* (2006.01)

(52) U.S. Cl.
CPC ........ *A61B 5/14546* (2013.01); *A61B 5/7221* (2013.01); *A61B 5/1451* (2013.01); *G01N 27/3271* (2013.01)

(56) References Cited

U.S. PATENT DOCUMENTS

| | | | |
|---|---|---|---|
| 5,798,031 A | 8/1998 | Charlton et al. | |
| 5,857,462 A | 1/1999 | Thomas et al. | |
| 6,129,823 A | 10/2000 | Hughes et al. | |
| 6,360,888 B1 | 3/2002 | McIvor et al. | |
| 8,219,174 B2* | 7/2012 | Feldman | A61B 5/0024 600/345 |
| 2003/0146113 A1 | 8/2003 | Unkrig et al. | |
| 2005/0004439 A1 | 1/2005 | Shin et al. | |
| 2005/0013731 A1 | 1/2005 | Burke et al. | |
| 2005/0123441 A1 | 6/2005 | Unkrig et al. | |
| 2005/0272985 A1* | 12/2005 | Kotulla | A61B 5/14503 600/309 |
| 2008/0242962 A1 | 10/2008 | Roesicke et al. | |
| 2008/0249384 A1 | 10/2008 | Skyggebjerg et al. | |
| 2011/0184267 A1 | 7/2011 | Duke et al. | |
| 2012/0078071 A1 | 3/2012 | Bohm et al. | |
| 2012/0191362 A1 | 7/2012 | Schmitt et al. | |
| 2012/0215462 A1 | 8/2012 | Goode, Jr. et al. | |
| 2014/0100435 A1 | 4/2014 | Duke et al. | |
| 2014/0121989 A1 | 5/2014 | Kamath et al. | |
| 2014/0182350 A1* | 7/2014 | Bhavaraju | A61B 5/1495 73/1.02 |
| 2016/0162662 A1 | 6/2016 | Monirabbasi et al. | |
| 2016/0354543 A1* | 12/2016 | Cinar | A61B 5/14532 |

FOREIGN PATENT DOCUMENTS

| | | |
|---|---|---|
| CN | 102821687 A | 12/2012 |
| CN | 103732130 A | 4/2014 |
| CN | 104434311 A | 3/2015 |
| CN | 104434312 A | 3/2015 |
| CN | 104605862 A | 5/2015 |
| CN | 104755019 A | 7/2015 |
| CN | 105046042 A | 11/2015 |
| CN | 105342629 A | 2/2016 |
| CN | 105408902 A | 3/2016 |

OTHER PUBLICATIONS

Shanthi et al., Neural Network Based Filter for Continuous Glucose Monitoring: Online Tuning with Extended Kalman Filter Algorithm, WSEAS Transactions on Information Science and Applications, 2012, pp. 199-209, vol. 9, issue 7.

* cited by examiner

METHOD FOR PROVIDING A SIGNAL QUALITY DEGREE ASSOCIATED WITH AN ANALYTE VALUE MEASURED IN A CONTINUOUS MONITORING SYSTEM

RELATED APPLICATIONS

This application is a continuation of U.S. Ser. No. 16/229,322 filed on Dec. 21, 2018 which is a continuation of PCT/EP2017/065942, filed on Jun. 28, 2017, which claims priority to EP 16 176 940.1, filed on Jun. 29, 2016, the entire disclosures of all of which are hereby incorporated herein by reference.

BACKGROUND

The present disclosure relates to a method for providing a signal quality degree associated with an analyte value measured in a continuous monitoring system as well as to related methods for determining an amount of insulin to be delivered and for calibrating the continuous monitoring system. The present disclosure further relates to a computer program product as well as to a sensor unit and to a continuous monitoring system which apply at least one of the mentioned methods.

The methods and devices according to the present disclosure may primarily be used for a continuous monitoring of the analyte glucose, wherein analyte values are measured by a biosensor in an interstitial fluid subcutaneously and/or in vivo, wherein the biosensor is implantable or partially implantable. The methods and devices according to the disclosure may be applied both in the field of home care as well as in the field of professional care, such as in hospitals. However, other applications are also feasible.

Monitoring certain body functions, more particularly monitoring one or more concentrations of certain analytes, plays an important role in the prevention and treatment of various diseases. Without restricting further possible applications, the methods and devices according to the disclosure are described in the following with reference to a continuous monitoring of the analyte glucose in an interstitial fluid by using a biosensor.

The glucose monitoring may be performed by using electrochemical sensors as well as optical measurements. Examples of electrochemical biosensors for measuring glucose, specifically in blood or other body fluids, are known from U.S. Pat. Nos. 5,413,690 A, 5,762,770 A, 5,798,031 A, 6,129,823 A and US 2005/0013731 A1. For example, an active sensor region is directly applied to a measurement site which is, generally, arranged in an interstitial tissue, and may convert glucose into an electrically charged entity by using an enzyme, in particular into glucose oxidase, generally abbreviated to "GOD." As a result, the detectable charge in the electrochemical biosensor may be related to the glucose concentration and can, thus, be used as a measurement variable. Examples of such kinds of transcutaneous measurement systems are described in U.S. Pat. No. 6,360,888 B1 or US 2008/0242962 A1.

As generally known, glucose measurements may be performed as "spot measurements." For this purpose, a sample of a body fluid is taken from a user, i.e., a human or an animal, in a targeted fashion and examined with respect to the analyte concentration in vitro and/or in a transdermal fashion. In contrast, the continuous measuring of the analyte glucose in the interstitial fluid, also referred to as "continuous glucose monitoring" or abbreviated to "CGM," has been established as a method for managing, monitoring, and controlling a diabetes state. For this purpose, the continuous measuring of the analyte value in the interstitial fluid is performed via a transcutaneous or a subcutaneous system in a subcutaneous fashion and/or in vivo. Accordingly, the biosensor or at least a measuring portion thereof may be arranged under the skin of the user. Generally, an evaluation and control part of the system, also referred to as a "patch," may be located outside the body of a user. The biosensor is generally applied by using an insertion instrument, which is, in an exemplary fashion, described in U.S. Pat. No. 6,360,888 B1. However, other types of insertion instruments are also known. Further, a control part may be required. Such a control part may be located outside the body and have to be in communication with the biosensor. Generally, communication is established by providing at least one electrical contact between the biosensor and the control part, wherein the contact may be a permanent electrical contact or a releasable electrical contact. Other techniques for providing electrical contacts, such as by using appropriate spring contacts, are known and may also be applied.

In continuous glucose measuring systems, the concentration of the analyte glucose may be determined by employing an electrochemical sensor comprising an electrochemical cell having a working electrode and a counter electrode. Herein, the working electrode may have a reagent layer comprising an enzyme with a redox active enzyme co-factor adapted to support an oxidation of the analyte in the body fluid. The reagent layer may, further, comprise or redox mediator which, typically, may act as an electron acceptor. The redox mediator can react with the enzyme co-factor and may, thus, transport electrons received from the enzyme co-factor to a counter electrode surface, such as by diffusion. At the counter electrode surface, the redox mediator may be oxidized and the transferred electrons can, consequently, be detected as a current. The current may, preferably, be related to a concentration of the analyte in the body fluid, e.g., such as being proportional thereto. US 2003/0146113 A1 and US 2005/0123441 A1 disclose examples for this process.

According to S. Shanthi and D. Kumar, *Neural Network Based Filter for Continuous Glucose Monitoring: Online Tuning with Extended Kalman Filter Algorithm*, WSEAS Transactions on Information Science and Applications Vol. 9, 2012, p. 199-209, an evaluation of the accuracy of continuous glucose monitoring (CGM) systems is complex for two primary reasons. First, the CGM systems assess fluctuations of the blood glucose level indirectly by measuring the concentration of interstitial glucose but are calibrated via self-monitoring in order to approximate the blood glucose level. Second, CGM data reflect an underlying process in time and usually consist of ordered-in-time highly interdependent data points. Apart from a physiological time lag and an improper calibration, random noise and errors, in particular due to sensor physics and sensor chemistry, might affect the accuracy of the CGM data. As a result, the performance of CGM signals, in particular with respect to a hypoglycemic alert generation and to a control input into an artificial pancreas, may be deteriorated. Related studies have shown that the percentage of false alarms and missing alarms is about 50 percent, which the authors primarily assign to insufficient filtering.

US 2008/249384 A1 discloses glucose monitoring systems for continuously measuring the glucose concentration in a patient's blood. The system is adapted to communicate with one or more sensors for transcutaneous insertion into a patient and for producing sensor signals related to the glucose concentration. The system comprises an electronic calculator unit and a display for displaying the measured glucose concentration. The electronic calculator unit further comprises means for calculating an estimate of the uncertainty, i.e., the degree of accuracy of the glucose measurement, and the display is configured for displaying an interval representing the uncertainty.

US 2005/004439 A1 discloses a method of calibrating glucose monitor data including collecting the glucose monitor data over a period of time at predetermined intervals. It also includes obtaining at least two reference glucose values from a reference source that temporally correspond with the glucose monitor data obtained at the predetermined intervals. Also included is calculating the calibration characteristics using the reference glucose values and corresponding glucose monitor data to regress the obtained glucose monitor data. And, calibrating the obtained glucose monitor data using the calibration characteristics. In preferred embodiments, the reference source is a blood glucose meter, and the at least two reference glucose values are obtained from blood tests. In additional embodiments, calculation of the calibration characteristics includes linear regression and, in particular embodiments, least squares linear regression. Alternatively, calculation of the calibration characteristics includes non-linear regression. Data integrity may be verified and the data may be filtered.

US 2014/121989 A1 discloses systems and methods for measuring an analyte in a host. More particularly, the disclosure relates to systems and methods for processing sensor data, including calculating a rate of change of sensor data and/or determining an acceptability of sensor or reference data.

US 2012/215462 A1 discloses systems and methods for processing sensor analyte data, including initiating calibration, updating calibration, evaluating clinical acceptability of reference and sensor analyte data, and evaluating the quality of sensor calibration. During initial calibration, the analyte sensor data is evaluated over a period of time to determine stability of the sensor. The sensor may be calibrated using a calibration set of one or more matched sensor and reference analyte data pairs. The calibration may be updated after evaluating the calibration set for best calibration based on inclusion criteria with newly received reference analyte data. Fail-safe mechanisms are provided based on clinical acceptability of reference and analyte data and quality of sensor calibration. Algorithms provide for optimized prospective and retrospective analysis of estimated blood analyte data from an analyte sensor.

S. Shanthi et al., s. o., deal with a removal of errors due to various noise distributions in CGM sensor data. A feed forward neural network is trained with an Extended Kalman Filter algorithm to nullify the effects of white Gaussian, exponential and Laplace noise distributions in CGM time series. The process and measurement noise covariance values incoming signal. This approach answers for an interperson and intra-person variability of blood glucose profiles. The neural network updates its parameters in accordance with a signal-to-noise-ratio of the incoming signal. The performance of the proposed system is analyzed with root mean square as a metric and has been compared with previous approaches in terms of time lag and smoothness relative gain. The new mechanism enables the application of CGM signals to hypoglycemic alert generation and input to an artificial pancreas.

US 2014/182350 A1 discloses a method for determining an end of life of a CGM sensor which includes evaluating a plurality of risk factors using an end of life function to determine an end of life status of the sensor and providing an output related to the end of life status of the sensor. Thus, this method is directed to solving the problem of determining the status or time for which the end of life of a sensor is near, so that a user may be informed that the sensor should be changed. The plurality of risk factors are selected from a list including a number of days the sensor has been in use, whether there has been a decrease in signal sensitivity, whether there is a predetermined noise pattern, whether there is a predetermined oxygen concentration pattern, and an error between reference BG values and EGV sensor values. For this purpose, quality metrics are scaled according to pre-determined weights and combined to produce an indicator of the overall quality of the computed glucose value, wherein the weights may be applicable to every metric and may show how indicative a metric is of end of life.

The present disclosure provides a method for providing a signal quality degree associated with an analyte value measured in a continuous monitoring system, a method for determining an amount of insulin to be delivered, a method for calibrating the continuous monitoring system, a computer program product, a sensor unit, and a continuous monitoring system which at least partially avoid the shortcomings of known methods and devices of this kind and which at least partially address the above-mentioned challenges.

In particular, it is desired that the methods and devices according to the present disclosure may be capable of providing a signal quality degree associated with a measured glucose which can be used in a decision whether an actually measured glucose value to which the signal quality degree is associated with may be considered in providing a specific signal by the continuous monitory system or not. For this purpose, it is, particularly, desired to implement a process which may be adapted of consecutively acquiring measured data and providing associated signal quality information, preferably in a nearly real, real-time or quasi-continuous approach, especially without user interaction, during the lifetime of the biosensor. The signal quality degree may also be able to assume a value between 0 and 1, wherein the value of 0 describes an insufficient quality while the value of 1 refers to a sufficient quality. In particular, it is desired that the signal quality degree may allow providing an improved accuracy value for use as a control input into an artificial pancreas and/or for a hypoglycemic alert generation throughout the lifetime of the biosensor.

SUMMARY

The present application discloses a method for providing a signal quality degree associated with an analyte value measured in a continuous monitoring system, a method for determining an amount of insulin to be delivered, a method for calibrating the continuous monitoring system, a computer program product, a sensor unit, and a continuous monitoring system. The disclosed methods and systems may additionally include the individual features or various combination of the features described herein.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "preferably," "more preferably," "particularly," "more particularly," "specifically," "more specifically" or similar terms are used in conjunction with optional features, without restricting alternative possibilities. Thus, features introduced by these terms are generally optional features and are not intended to restrict the scope of the invention in any way. The various embodiments may, as the skilled person will recognize, be performed by using alternative features. Similarly, features introduced by "in an embodiment" or similar expressions are intended to be optional features, without any restriction regarding alternative embodiments, without any restrictions regarding the scope of the invention and without any restriction regarding the possibility of combining the features introduced in such way with other optional or non-optional features.

In a first embodiment, a method for providing a signal quality degree associated with an analyte value measured in a continuous monitoring system is disclosed. Herein, the method comprises the following method steps as listed below:

a) receiving a measured analyte value from a biosensor, wherein the biosensor is adapted for measuring the analyte values, and wherein the biosensor is comprised in a continuous monitoring system or controlled by the continuous monitoring system;

b) determining at least two impact parameters, wherein each of the impact parameters is influenced by an operational status of the continuous monitoring system, and wherein each of the impact parameters is capable of exerting an influence on a signal quality of the biosensor, wherein the influence of each of the impact parameters on the signal quality of the biosensor is expressed by a weight being assigned to each of the impact parameters; and c) determining the signal quality degree associated with the measured analyte value by combining the weights and the corresponding impact parameters; and providing the signal quality degree associated with the analyte value.

The indicated steps may, preferably, be performed in the given order, thereby starting with step a). However, any or all of the indicated steps may also be preformed at least partially concurrently, such as over a definite period of time. Additionally, the indicated steps as a whole may also be repeated several times in order to achieve a subsequent determination of the signal quality degree, such as after a prespecified time or in consequence of an occurrence of a prespecified event. Further, additional method steps, whether described herein or not, may be performed, too.

The methods according to the present disclosure may be computer-implemented methods. As generally used, the term "computer-implemented" indicates that performing the method involves using a processing module, such as a processing module as comprised in a computer, in a computer-assisted system, in a computer network, or in another programmable apparatus, whereby any or all features of the method steps may be performed by employing a computer program being adapted for a use in the processing module. For the purpose of the present disclosure, the processing module may be comprised in the continuous monitoring system, may be controlled by the continuous monitoring system, may be controlling the continuous monitoring system, and/or may be at least communicating with the continuous monitoring system. As will be explained later in more detail, the processing module may, thus, be comprised in an electronics unit and/or in a receiver of the continuous monitoring system.

According to step a) described above, the biosensor which is adapted for measuring the analyte values consecutively provides a plurality of measured analyte values which are received by the continuous monitoring system. As generally used, the terms "biosensor" or "CGM sensor" refer to an arbitrary device being configured for conducting at least one medical analysis. For this purpose, the biosensor may be an arbitrary device configured for performing at least one diagnostic purpose and, specifically, comprising at least one analyte sensor for performing the at least one medical analysis. The biosensor may, specifically, comprise an assembly of at least two components being capable of interacting with each other, such as in order to perform one or more diagnostic purposes, such as in order to perform the medical analysis. The components may be capable of performing at least one detection of the at least one analyte in the interstitial fluid and/or in order to contribute to the at least one detection of the at least one analyte in the interstitial fluid. Further, the biosensor may be connectable to an evaluation device, such as to an electronics unit. For the purposes of the present disclosure, the biosensor may either constitute a part of the continuous monitoring system or not. In the latter case the biosensor may, however, be controlled by the continuous monitoring system, for example, by using a receiver and/or an electronics unit of the continuous monitoring system.

In one embodiment, the biosensor may be a fully implantable biosensor or a partially implantable biosensor which may be adapted for performing the detection of the analyte in the body fluid in a subcutaneous tissue, for example, in an interstitial fluid. As used herein, the terms "implantable biosensor" or "transcutaneous biosensor" may refer to an arbitrary biosensor being adapted to be fully or at least partly arranged within the body tissue of the patient or the user. For this purpose, the biosensor may comprise an insertable portion. Herein, the term "insertable portion" may generally refer to a part or component of an element configured to be insertable into an arbitrary body tissue. The biosensor may fully or partially comprise a biocompatible surface, i.e., a surface which may have as little detrimental effects on the user, the patient, or the body tissue as possible, at least during typical durations of use. For this purpose, the insertable portion of the biosensor may have a biocompatible surface. As an example, the biosensor, specifically the insertable portion thereof, may fully or partially be covered with at least one biocompatible membrane, such as a polymer membrane or a gel membrane which, on one hand, may be permeable for the body fluid or at least for the analyte as comprised therein and which, on the other hand, may retain sensor substances, such as one or more test chemicals within the sensor, thus preventing a migration thereof into the body tissue. Other parts or components of the biosensor may remain outside of the body tissue.

As generally used here, the term "patient" refers to a human being or to an animal, independent of whether the human being or the animal, respectively, may be in a healthy condition or may suffer from one or more diseases. Further, the term "user" may refer to a human being, whether being the patient or not, or, to a computer-assisted system which may be capable of receiving and/or interpreting any values, whether being measured values or values directly or indirectly determined therefrom. As an example, the user may be a human being suffering from diabetes or, in addition or as an alternative, a person or a computer-assisted system being in charge of supervising the patient. Alternatively, or additionally, the disclosure may also be applicable to other types of users or patients or diseases.

As used herein, the term "body fluid" may, generally, refer to a fluid, in particular a liquid, which may typically be present in a body or a body tissue of the user or the patient and/or which may be produced by the body of the user or the patient. The body fluid may be selected from the group consisting of blood and interstitial fluid. However, additionally or alternatively, one or more other types of body fluids may be used, such as saliva, tear fluid, urine or other body fluids. During the detection of analyte, the body fluid may be present within the body or body tissue. Thus, the biosensor may, specifically, be configured for detecting the analyte within the body tissue.

As further used herein, the term "analyte" may refer to an arbitrary element, component, or compound being present in the body fluid, wherein the presence and/or the concentration of the analyte may be of interest to the user, the patient, or to a medical staff, such as to a medical doctor. Particularly, the analyte may be or may comprise at least one arbitrary chemical substance or chemical compound which may participate in the metabolism of the user or the patient, such as at least one metabolite. As an example, the analyte may be selected from the group consisting of glucose, cholesterol, triglycerides, lactate. Additionally or alternatively, however, other types of analytes may be used and/or any combination of analytes may be determined. The detection of the analyte may be an analyte-specific detection. Without restricting further possible applications, the present disclosure is discussed herein with reference to a continuous monitoring of glucose in an interstitial fluid.

As used herein, the term "measured analyte value" refers to a result as acquired by a process of generating at least one signal, in particular at least one measurement signal, which characterizes an outcome of a measurement with respect to a property of the analyte. According to the present disclosure, the measured analyte value is received from the biosensor, wherein the term "receiving" refers to a process by which the continuous monitoring system obtains access to the at least one measured analyte value for further processing. Specifically, the at least one measured analyte value may be or may comprise at least one electronic signal, such as at least one voltage signal and/or at least one current signal which may be transferred from the biosensor to the continuous monitoring system. The at least one measured analyte value may be or may comprise at least one analogue measured value and/or may be or may comprise at least one digital measured value.

As used herein, the term "continuous monitoring" refers to a process of consecutively acquiring data and deriving desired information therefrom, preferably in a nearly real, real time or quasi-continuous approach, for frequently providing and/or updating the measured analyte values, in particular without user interaction. For this purpose, a plurality of measured analyte values are generated and evaluated, wherefrom the desired information is determined. The plurality of the measured analyte values may be recorded within fixed or variable time intervals or, alternatively or in addition, at an occurrence of at least one prespecified event. As an example, an analyte value may routinely be recorded every minute, wherein in the event that an actually recorded analyte value may deviate from a previous analyte value above a threshold, the time interval may, however, be set to 10 seconds. Other examples depending on the circumstances of the patient or user may be feasible. In particular, the biosensor according to the present disclosure may be adapted for the continuous monitoring of one or more analytes, in particular of glucose, such as for managing, monitoring, and controlling a diabetes state.

According to step b) set forth above, at least two impact parameters are determined. As used herein, the term "determining" relates to a process of generating at least one representative result, such as a plurality of representative results, which may be acquired by evaluating the at least one measured analyte value, wherein the term "evaluating" may refer to an application of methods for deriving the at least one representative result therefrom.

As used herein, the term "impact parameter" refers to a characteristic value of the continuous monitoring system, a part thereof, or a component which is controlled by the continuous monitoring system, for example, the biosensor. Preferably, only those characteristic values are considered which, first, are influenced by an operational status of the continuous monitoring system and which, second, are able to exert an influence on a signal quality of the biosensor. Preferably, at least two impact parameters, alternatively, two, three, four, five, six or more impact parameters, are used for the determination of the signal quality degree which is associated with the measured analyte value. As described below in more detail, such characteristic values are, preferably, considered which are capable of providing temporary information about the operational status of the continuous monitoring system during the lifetime of the biosensor.

The influence of each of the impact parameters may exert on the signal quality of the biosensor is expressed by a weight that is assigned to each of the impact parameters. As generally used, the term "weight" refers to a contribution each of the at least two impact parameters may have on the signal quality of the biosensor. Thus, each of the impact parameters may be adjusted with respect to its contribution to influencing the signal quality of the biosensor rather assuming an equal contribution of all chosen impact parameters to a final result. Herein, the weight assigned to each impact parameter may be determined from previously recorded data and a corresponding variance thereof for the respective impact parameter. Thus, the weight may be expressed in form of a numerical value, such as a numeral having a positive or a negative sign. Examples for the weights may be found below. Alternatively, the weight may be expressed in form of a percentage, wherein the percentages for the weights for all selected input parameters may or may not sum up to 100%. However, other embodiments may be equally feasible. In particularly preferred embodiment, a specific weight may be assigned to each of the selected impact parameters by employing a retrospective analysis of selected measured analyte values as received from the biosensor, such as by performing tests with the biosensor, in particular, by acquisition of measured analyte values by using the biosensor under known prespecified conditions of the continuous monitoring system.

As used herein, the term "operational status" of the continuous monitoring system refers to at least one measurable property of the continuous monitoring system, of a part thereof, or of a component being controlled by the continuous monitoring system, e.g., the biosensor, wherein the measurable property is capable of temporarily influencing at least one of the impact parameters. As a result, the operational status of the continuous monitoring system may be subject to a temporal variation, wherein the operational status which pertains simultaneously at the time at which the measured analyte value is received by the continuous monitoring system may, preferably, be denoted as "current operational status" and considered for the further processing, in particular, for determining the amount of insulin to be provided to the patient, such as by implementing a CGM augmented bolus. Consequently, the operational status of the continuous monitoring system is neither limited to an end of life status of the biosensor nor only capable of providing an output related to the end of life status of the biosensor. Rather, the operational status refers to, permanently or intermittently, provided information related to a temporary value of the at least one measurable property of the continuous monitoring system.

The at least two impact parameters may be selected from the following list which includes impact parameters which may be considered as being influenced by the operational status of the continuous monitoring system:
  at least one parameter related to a Kalman filter;
  a current wear time of the biosensor;
  a current age of the biosensor;
  a current concentration range;
  a deviation from a mean analyte value;
  a current rate of change;
  at least one quantity related to a calibration of the biosensor;
  a current failure probability;
  a current potential of a counter electrode;
  at least one process parameter of the production of the biosensor;
  a sensitivity of the biosensor; and
  at least one impedance value of the biosensor.

It may be emphasized that while all of the impact parameters in this list are capable of providing information about the current operational status of the continuous monitoring system, some of the impact parameters in this list appear intrinsically as not being capable of providing an output which could be related to the end of life status of the biosensor. In particular, the current failure probability, the at least one process parameter of the production of the biosensor, and the at least one quantity related to the calibration of the biosensor, appear not capable of contributing to the end of life status of the biosensor in a reasonable manner.

Investigations with existing continuous monitoring system have shown that a selection of the at least two impact parameters from the following list may be effective for determining the signal quality degree of the corresponding continuous monitoring system:
  the (1,1) element of a covariance matrix of the Kalman filter;
  the current rate of change;
  the current potential of a counter electrode;
  the current wear time of the biosensor;
  a time passed since the last calibration of the biosensor; and
  a sensitivity and/or admittance of the biosensor.

In a first embodiment, a parameter related to the covariance matrix of a Kalman filter, in particular an element thereof, more particular the (1,1) matrix element thereof, may be selected as one of the impact parameters. However, the other matrix elements thereof may also be used for this purpose. As generally used, the term "Kalman filter" refers to an algorithm which uses a plurality of measured values that may comprise measurement inaccuracies and generates estimates of more accurate variables compared to a single measurement alone. Preferably, the algorithm may work in a two-step process, wherein, in a first step, the Kalman filter may generate estimates of the current variables along with their accuracy. In a next step, values acquired in a subsequent measurement may be used for updating the estimates, such as by using a weighted average, wherein a higher weight may be assigned to estimates comprising a higher certainty. Since the algorithm is recursive, it may be used for real-time processing, whereby it may be sufficient to use the present measured value, the previously estimated values, and an accuracy matrix. Thus, the Kalman filter is applied in the field of data processing, in particular as described in US 2012/191362 A1, the content of which is incorporated here by reference. When applying the Kalman filter, the covariance matrix of the Kalman filter may be employed as one of the impact parameters for deriving the signal quality since it provides a measure for an uncertainty in filtering.

In a further embodiment, the current wear time of the biosensor may be selected as one of the impact parameters. The current wear time may be determined by a time interval after an application of the biosensor to the user. In this regard, the time of application of the biosensor to the user may be determined by detecting the time when an electrical circuit that involves the biosensor is completed. By way of example, by applying a transmitter to a body mount which comprises the biosensor the electrical circuit that involves the biosensor can be completed. The current wear time of the biosensor may be suitable for this purpose, in particular, since the biosensor may comprise a membrane which may be soaked with interstitial fluid, to a large extent, in order to achieve an enhancement of the analyte diffusion within the biosensor. In order to allow determining a specific weight that may be assigned to the current wear time as one of the selected impact parameters, the influence of the wear time may be determined in tests of the biosensor, which may, preferably, be performed in vitro, in vivo may also be possible. As a result, the contribution of the current wear time to the signal quality degree may be modeled as a function.

In a further embodiment, the current age of the biosensor may be selected as one of the impact parameters. The current age of the biosensor may be determined by considering a time interval after the production of the biosensor has been concluded. The current age of the biosensor may be suitable for this purpose since the biosensor may be subject to a degradation which may occur in one or more components of the biosensor independent of a frequency and/or a modality of its actual use.

In a further embodiment, the deviation of the actually measured analyte value from the mean analyte value may be selected as one of the impact parameters. As generally used, the term "mean analyte value" refers to a mean value derived max which is derived from a number of already measured analyte values. The deviation from the mean analyte value may be determined by comparing the measured analyte value with a mean value which may be derived from a number of previously measured analyte values. By way of example, an arithmetic mean may be considered, wherein an average obtained by the sum of the values divided by the number of values may be determined. However, other kinds of means, such as a median or geometric mean, may also be employed here.

In a further embodiment, the current concentration range with respect to the actually measured analyte value may be selected as one of the impact parameters. The current concentration range may be determined by a concentration of the analyte within in the interstitial fluid of the user. The current concentration range may be suitable for this purpose since it may influence the signal quality in the following manner. On one hand, a low analyte concentration may exhibit a low signal-to-noise ratio since less analyte may diffuse through the membrane of the biosensor while an amount of one or more interferents may remain unmodified. As used herein, the low analyte concentration may refer to a concentration range from 0 to 100 mg/dl, from 0 to 60 mg/dl, from 0 to 50 mg/dl, or from 0 to 40 mg/dl. On the other hand, at very high concentration ranges the sensor may enter a reaction product limited regime in which the analyte may no longer be completely converted into a current. This effect may, in particular, occur in the case in which glucose oxygen may be the reaction product. As used herein, the high concentration may refer to a concentration range from 140 to 400 mg/dl, from 160 to 400 mg/dl, or from 200 to 400 mg/dl. Similarly to the current wear time, a specific weight that may be assigned to the current concentration range as one of the selected impact parameters, may be determined in tests of the biosensor, which may be performed in vitro and wherein in vivo may also be possible. As a result, the contribution of the current concentration range to the signal quality degree may, thus, be modeled as a function of the current concentration.

In a further embodiment, the current rate of change of the actually measured analyte value may be selected as one of the impact parameters. The current rate of change may be determined by recording a temporal alteration of the measured analyte value. In general, the current rate of change may provide a larger contribution to the inaccuracy of the measured value the faster the measured value changes. Not wishing to be bound by theory, this effect may be based on an observation that a time lag between a concentration change in the interstitial fluid and the subsequent concentration change in the blood may rise with increasing rate of change. Typically, any rate of change which may exceed a value of 0.5 mg/(dl·min), of 1.0 mg/(dl·min), or of 2 mg/(dl·min), may be taken into account. Similarly as above, a specific weight that may be assigned to the current rate of change as one of the selected impact parameters may be determined in tests of the biosensor, which may, preferably, be performed in vitro and wherein in vivo may also be possible. As a result, the contribution of the current rate of change to the signal quality degree may, thus, be modeled as a function.

In a further embodiment, a parameter related to the calibration of the biosensor may be selected as one of the impact parameters, such as the number of valid calibrations of the biosensor or the time which may have passed since the last calibration. The time passed since the last calibration may be determined by recording the time at which a calibration event is performed, wherein the signal quality degree may decrease with increasing time after the last calibration event. Alternatively or in addition, the number of valid calibration values may be determined by counting calibration values which were successfully obtained with the biosensor within a defined time interval in the past, preferably with little deviation and at slow rates of change. Additionally, it is possible to only consider such calibration values as valid calibration values which have been acquired during a recent period of time, wherein the term "recent" may refer to an adjacent period of time, such as the last day, the last two days prior, or the last week to the time of performing the method. Consequently, the signal quality may be considered to increase with an increasing number of valid calibration values.

In a further embodiment, the current failure probability of the biosensor may be selected as one of the impact parameters. Herein, the current failure probability may be determined by taking into account a dropout probability of the biosensor, to which a value from 0 to 1 may be assigned. A dropout which can directly be determined from a measuring signal may occur in an event in which the measuring signal may decrease rapidly in a non-physiological manner. A higher value for the current failure probability may indicate that a dropout of the biosensor may appear more likely, thus, resulting in a lower signal quality.

In a further embodiment in which the biosensor may be an electrochemical sensor comprising an electrochemical cell having at least one working electrode and a counter electrode, wherein a predefined electrical potential may be applied between the working electrode and the counter electrode, the current potential of the counter electrode may be selected as one of the impact parameters. For this purpose, the current potential of the counter electrode may be determined by recording a deviation from the predefined electrical potential. Typically, the potential at the counter electrode may be balanced versus the working electrode by using a potentiostat and keeping it at a constant level. As used herein, the term "potentiostat" refers to an electronic device being adapted for adjusting and/or measuring a voltage difference between the working electrode and the counter electrode within the electrochemical cell. Alternatively, the electrochemical cell of the biosensor may, additionally, include a reference electrode, wherein the electrical potential of the working electrode may be kept constant with respect to the reference electrode by using the potentiostat and wherein the counter electrode may provide for a current compensation at the working electrode. For this purpose, the reference electrode can be driven within a typical operational mode comprising preset lower and upper limits as corresponding thresholds. Consequently, exceeding a prespecified threshold with respect to the preset limits may indicate a lesser signal quality. Similarly as above, a specific weight that may be assigned to the potential of the counter electrode as one of the selected impact parameters may be determined in biosensor tests which may, preferably, be performed in vitro and wherein in vivo may also be possible. As a result, the contribution of the potential of the counter electrode to the signal quality degree may, thus, be modeled as a function.

In this further embodiment, a sensitivity value and/or an impedance value related to the biosensor may be selected as one of the impact parameters. The "sensitivity value" may be determined by measuring a raw current I of the biosensor, whereby a concentration c of an analyte, such as of glucose, may be taken into account. By way of example, the sensitivity S of the biosensor may show a linear relationship for the concentration c, such as below an empirical value of 100 mg/dl to 150 mg/dl for the analyte glucose but exhibit a more complex curvature for concentrations above this empirical value. Further, the term "impedance value" may refer to at least one value derived from an impedance spectrum of the biosensor, in particular, one or more components of a complex resistance, e.g., an admittance Y value at one or more different frequencies. It may be preferable to measure the DC raw current I for determining the sensitivity S of the biosensor while the complex admittance Y or a value related thereto can, preferably, be determined by using an AC circuit adapted for this purpose. However, one or more other values as derived from the impedance spectrum may also be feasible.

By providing a relationship between the sensitivity S and the admittance Y of the biosensor, a sensitivity-to-admittance relation, such as a ratio S/Y, may be determined. The sensitivity-to-admittance relation can, preferably, be used to acquire information about a current state of intrinsic transport properties of the membrane of the biosensor while geometric properties of the membrane, such as a swelling of the membrane during the operation of the biosensor, can be disregarded. Thus, the sensitivity-to-admittance relation may remain constant during the operation of the biosensor such that no in-vivo drift can occur in the biosensor, as long as the biosensor is diffusion-controlled, i.e., as long as a reaction rate of the analyte is considerably higher compared to a diffusion rate of the analyte.

In addition to the sensitivity-to-admittance relation, further impact parameters may be used which can be determined by measuring the admittance Y of the biosensor, in particular, an electrical capacitance C of the biosensor, an electrical resistance $R_M$ of the membrane, and/or a time constant r which may be obtained by the relation $r=R_M \cdot C$. Further impact parameters may also be feasible.

According to step c) described above, a signal quality degree is determined by evaluating the measured analyte value by combining at least two individual weights which are each assigned to a corresponding one of the at least two of the impact parameters. As generally used, the terms "signal quality degree" or "signal quality measure" refer to a numerical value which may be suitable to indicate an accuracy of the analyte value as measured by the biosensor, wherein the accuracy of the biosensor is usually considered as a closeness of the measured value of a quantity of the analyte to a true value of the quantity of the analyte. In this regard, the measured analyte values as provided by each continuous monitoring system may each comprise a measurement error, wherein the measurement error may be defined as a relative standard deviation (SRD) between the measured analyte values and corresponding reference analyte values. The relative standard deviation (SRD) may be one possible metric being applicable for representing the measurement error. Alternatively or in addition, an absolute relative deviation (ARD), an absolute deviation (AD), or a standard deviation (SD) may also be employed for this purpose. As a result, the signal quality degree may be reciprocally related to the measurement error that may be expected for a measured analyte value such that no expected measurement error may be expressed as a high signal quality degree while a large expected measurement error may be expressed as a low signal quality degree. For practical reasons, the signal quality degree may, preferably, assume a numerical value that may be selected from a predefined numerical range, such as between a lower threshold indicating complete inaccuracy and a higher threshold indicating complete accuracy. By way of example, the signal quality degree may assume a numerical value between 0 and 1 or, alternatively, between 0% and 100%. However, other relationships between the signal quality degree and the accuracy may also be feasible.

In some embodiments, it may be advantageous to set the signal quality degree to a zero value, i.e., to indicate signal quality as completely inaccurate, over a prespecified period of time in case a particular event, in particular an event having a high priority, may occur. Consequently, the signal quality may already be set to zero in case one of the high priority events assumes a zero value, thus, allowing a fast treatment of specific events in determining the signal quality. The prespecified period of time may be selected to at least cover a period of time that may exceed the actual period of time during which the event may happen. This kind of event may include an initialization procedure of the biosensor and/or of the continuous measuring system, such as over a prespecified period of time after the continuous measuring system and/or the biosensor may have been activated for measuring an analyte value and/or until predefined operational conditions of the continuous measuring system and/or the biosensor may have been achieved. This kind of event may also include untypical voltage and/or current values at one or more of the electrodes, such as unusual voltage values at the counter electrode, non-physiologically increasing current values, or current signals exhibiting a poor signal-to-noise ration. Other kinds of events may also be feasible. This embodiment may, thus, allow taking into account in a simple manner the kind of deviations that may likely occur during the corresponding event.

The accuracy of each of the measured analyte values may be determined in a reasonable approximation by combining the weights which are individually assigned to each of the impact parameters and the corresponding impact parameters. For this purpose, the weight for each of the impact parameters may, in a particularly preferred embodiment, be assigned to the signal quality degree by using a multivariate function. As generally used, the term "multivariate function" refers to a function adapted to derive at least one result from at least two variables. For this purpose, an arbitrary function for deriving at least one numerical result, also referred to as an output, from at least two variables, preferably from the weights and the individually assigned impact parameters, also referred to as input variables, may be used. The function may comprise an arbitrary rule for generating the output by using the at least two input variables. The multivariate function is, or may, comprise at least one equation, in particular a linear equation using the at least two variables, the weights and the individually assigned impact parameters, and a plurality of coefficients, thereby deriving the at least one result. The multivariate function may be or may include a one-step algorithm in which the weights and the individually assigned impact parameters are used as input variables for one and the same algorithm, such as using one and the same equation. Alternatively, the multivariate function may be or may include multiple steps, wherein, step-by-step, two or more algorithms are successively applied.

In a particularly preferred embodiment, the signal quality degree Q may be determined by using the multivariate function according to Equation (1):

$$Q = \Sigma^n_i w_i \cdot p_i, \tag{1}$$

wherein $w_i$ denotes the i-th weight assigned to the i-th impact parameter $p_i$, wherein the serial number i is a non-negative ascending natural number within a closed interval from 1 to n, wherein n denotes the number of the selected impact parameters. In this manner it may be ensured that an individual weight is assigned to each of the n impact parameters.

However, other kinds of combinations of the weights and the corresponding impact parameters may also be feasible.

Thus, in accordance with step c), the signal quality degree is provided as a parameter which is associated with the analyte value. In a particularly preferred embodiment, the signal quality degree determined in a manner as described above and/or below may, subsequently, be communicated to the user of the continuous monitoring system as a temporary parameter. In this regard, it may be particularly advantageous to, simultaneously or consecutively, communicate both the measured analyte value and the corresponding signal quality degree as will be described below in more detail. Thus, the user obtains the signal quality degree as a parameter which, at any given event where it is determined, is temporarily associated with the corresponding analyte value. As a result, the signal quality degree may be capable of accompanying the analyte value as measured throughout the lifetime of the biosensor, thereby, permanently or intermittently, providing an indication about the actual accuracy of the analyte value.

A method for determining an amount of insulin to be delivered is disclosed herein. In one embodiment, the method comprises the following method steps:

d) determining a signal quality degree by applying the method for providing a signal quality degree associated with an analyte value measured in a continuous monitoring system as described herein; and e) determining the amount of insulin from a data pair, wherein the data pair comprises the measured analyte value from the biosensor and the signal quality degree associated with the measured analyte value.

The indicated steps may be performed in the given order, thereby starting with step d). However, any or all of the indicated steps may also be preformed at least partially concurrently, such as over a definite period of time. Additionally, the indicated steps as a whole may also be repeated several times in order to achieve a subsequent determination of the signal quality degree, such as after a prespecified time or in consequence of an occurrence of a prespecified event. Further, additional method steps, whether described herein or not, may also be performed.

With respect to step d), reference may be made to the description of the method for providing a signal quality degree associated with an analyte value measured in a continuous monitoring system as described elsewhere in this document. In this regard, it may be mentioned that step d), thereby includes an application of steps a), b) and c) as described above.

According to step e), the amount of insulin is determined from a data pair, wherein the data pair comprises the measured analyte value from the biosensor and the signal quality degree associated with the measured analyte value. As generally known, the term "insulin" refers to a peptide hormone as normally generated by beta cells in the pancreas used for regulating a metabolism of carbohydrates and fats by promoting an absorption of glucose. The insulin is, however, used to medically treat one or more diseases, such as one or more kinds of diabetes mellitus, wherein the amount of insulin, which may also be denominated by the terms "dose" or "bolus," to be provided to the patient requires careful consideration. For the purpose of determining the amount of insulin, especially, for mimicking an artificial pancreas, one or more algorithms may be used, in particular, a bolus calculator for determining a single dose of insulin, a pLGS (predictive low glucose suspend) algorithm and/or a CTR (control to range) algorithm.

As used herein, the term "data pair" refers to plurality of data, wherein each measured analyte value is directly coupled to the associated signal quality degree in a fashion that both values are provided as a doublet for further processing, in particular for failsafe operation of the biosensor in the continuous monitoring system. Thus, not only the actual measured analyte value is taken into account for determining the actual amount of insulin to be provided to the patient but also the associated signal quality degree. In case a low signal quality may be reported, it may be advantageous to suppress or antedate warnings and/or alarms, particularly in order to avoid false alarms, thereby helping to prevent alarm fatigue in the patient. Taking into account the signal quality in this manner may, in particular, allow suppressing a hyperglycemic alarm being indicative of a, generally, non-hazardous excessive glucose concentration while a hypoglycemic alarm being indicative of an insufficient glucose concentration that may potentially perilous to the patient may, equally, be antedated. In regard of enhancing therapy decisions, further details may be found in US 2011/184267 A1 and US 2014/100435 A1, the content of which are incorporated here by reference.

In some embodiments, the data pair may, simultaneously or consecutively, be communicated to a user. As already mentioned above, this may be advantageous since not only the measured analyte value but also the associated signal quality degree of a measured analyte value can, therefore, be used in a decision whether an actually measured analyte value will be considered in providing a specific signal to the continuous monitoring system, e.g., for determining the amount of insulin to be provided to the patient. As a result, the signal quality degree may, thus, provide an improved accuracy value for the use as a control input into an artificial pancreas and/or for a hypoglycemic alert generation.

In a further embodiment, a method for calibrating the continuous monitoring system is disclosed. This method comprises the steps of determining at least one calibration factor by comparing at least one measured analyte value with a value for an analyte content and wherein a signal quality degree associated with the measured analyte value is determined by applying the method for determining the signal quality degree of an analyte value measured in a continuous monitoring system as described elsewhere in this document. Thus, a general relationship between the measured analyte value and the value for the analyte content may be acquired by considering the associated signal quality degree when applying the at least one calibration measurement. The general relationship can, for example, be reported in the form of one or more calibration curves. In this connection, the general relationship is to be understood to mean a rule for a plurality of different measured analyte values on the value for the analyte content, which rule describes how the value for the analyte content may influence the measured analyte value. The rule can be ascertained for a continuous range of values for the analyte content or else for a discontinuous range of respective values, for example, a quantity of values spaced apart from one another. Accordingly, the general relationship can, for example, include a pointwise assignment of multiple values, a calibration factor, a calibration curve, or calibration function to the corresponding influence.

For calibrating, the at least one measured analyte value is, further, weighted pursuant to its associated signal quality degree. In a particularly preferred embodiment, the at least one measured analyte value may only be used for calibrating in a case in which its associated signal quality degree exceeds a predefined quality threshold. By way of example, the calibration of the continuous monitoring system may only be performed in case the measured analyte value in question may exceed the predefined quality threshold. Consequently, the calibration the continuous monitoring system may only be performed with high quality measured analyte values. As a result, a smaller number of calibrations may be required for the continuous monitoring system.

In a further embodiment, at least two measured analytes values, preferably, two, three, four, five, six, eight, ten, or twelve measured analytes values, may be recorded and combined with their associated signal quality degrees. For this purpose, a mean value, preferably a median, of the selected number of the measured analyte values may be formed by weighting each of the measured analyte values with a corresponding value that may be based on the associated signal quality degree. By way of example, a median of the ten measured analyte values may be formed, whereby each of the ten measured analyte values may be weighted by its associated signal quality degree in order to be used for calibration purposes.

Accordingly, the calibration factor may be determined by using previous calibrations and weighing the calibration factors with the corresponding signal quality degrees. Thus, the calibration may be performed by determining the desired values in a plurality of test samples or calibration samples in which the value for the analyte content is known. For example, it may be possible to prepare test samples which have a definite concentration of the known analyte and on which the selected impact parameter may exert a definite influence. In this way, it may be possible to determine a quantity of triplets of values, which each may comprise a pair of values, wherein each data pair comprises the measured analyte value and the value for the analyte content, and the associated signal quality degree. The pairs of values can themselves describe the general relationship, or the general relationship can be ascertained, for example by means of a fit, wherein, the associated signal quality may be considered. In some cases, it may be possible, for the general relationship to be described by a straight line with respect to a certain axis, wherein the slope and axis intercept can be determined by using an appropriate fit. The straight line may then be used as a calibration curve. More complex calibration curves may also be possible, for example exponential functions and/or polynomials, which may better describe the mentioned relationship.

The general relationship, more particularly, the calibration curve or calibration function, can be stored in at least one data storage, for example, in a volatile and/or nonvolatile data storage, which may be connected to at least one evaluation unit, such as a data processing device. The evaluation unit can be configured to completely or partly carry out the method steps of the methods described herein. The calibration measurement can also be carried out in the evaluation unit or, alternatively, independently therefrom.

In another embodiment, a beneficial calibration interval may be determined by applying the signal quality degrees. As used herein, the term "beneficial calibration interval" may refer to a time interval at the end of which it may be recommended to perform a further evaluation procedure of the continuous monitoring system. As a result, the continuous monitoring system may, thus, always operate in a well-calibrated fashion. Hereby, the calibration and, hence, the accuracy of the continuous monitoring system can be enhanced.

Further, the beneficial calibration interval may be communicated to a user who may, thus, be capable of performing the further evaluation procedure soon afterwards. Alternatively, the continuous monitoring system may automatically perform the further evaluation procedure after the beneficial calibration interval unless a critical situation of the patient that may require immediately measuring further analyte values takes precedence.

Further, in an event in which the signal quality degree may fall below a first predefined quality threshold, an alarm may be suppressed and only activated after the signal quality degree meets a second predefined quality threshold. Herein, the second predefined quality threshold may be higher or lower compared to the first predefined quality threshold. Alternatively, in an event in which the signal quality degree may fall below a predefined quality threshold, an alarm may be antedated. These kinds of procedure may be advantageous in order to prevent alarm fatigue in the patient, wherein, the procedure may also depend on a consideration whether false positive or false negative alarms constitute a major problem in the relevant situation.

With respect to the biosensor, the measured analyte value, the signal quality degree, and the continuous monitoring system, reference may be made to the description of the method for providing a signal quality degree associated with an analyte value measured in a continuous monitoring system as described elsewhere in this document.

In a further aspect of the disclosure, a sensor unit is described. Herein, the sensor unit comprises a biosensor, an electronics unit, and a mountable patch. With respect to the biosensor, reference may be made to the description of the biosensor as described above and/or below.

As generally used, the term "electronics unit" refers to an arbitrary device having at least one electronic component. The electronics unit is adapted for performing any one of the methods according to the present disclosure, for example, the method for providing a signal quality degree associated with an analyte value measured in a continuous monitoring system. For this purpose, the electronics unit may include at least one electronic component for one or more of: performing a measurement with the biosensor, such as performing a voltage measurement or a current measurement; recording sensor signals; storing measurement signals or measurement data; and/or transmitting sensor signals or measurement data to another device. The electronics unit may specifically be embodied as a transmitter or may include a transmitter for transmitting data. Other embodiments of the electronic components are feasible.

Further, the term "mountable patch" generally refers to a device being adapted to receive both the biosensor and the electronics unit in a fashion that the sensor unit may be arranged hereby. For this purpose, the mountable patch may exhibit a connected state or a disconnected state, wherein, in the disconnected state, the sensor unit may not be operable. In the connected state, however, both the biosensor and the electronics unit may be connected by the mountable patch in a manner that the sensor unit may then be operable. Further, since the biosensor may be a fully implantable biosensor or a partially implantable biosensor adapted for performing the detection of the analyte in the body fluid in a subcutaneous tissue, e.g., in an interstitial fluid, the mountable patch may be arranged on the skin of the user. Thus, the sensor unit including the biosensor, the electronics unit, and the mountable patch may, generally, be worn on the body of the patient.

In a further embodiment, a continuous monitoring system is disclosed. Herein, the continuous monitoring system comprises a sensor unit and a receiver, wherein the sensor unit comprises a biosensor, an electronics unit, and a mountable patch, and wherein the electronics unit and/or the receiver is adapted to perform the method for providing a signal quality degree associated with an analyte value measured in a continuous monitoring system as described above. With respect to the sensor unit, the biosensor, the electronics unit, and the mountable patch, reference may be made to the description of the sensor unit as described above.

As described above, the sensor unit including the biosensor, the electronics unit, and the mountable patch may be considered a part of a body-worn portion of the continuous monitoring system. In contrast, the receiver may, generally, be considered as a handheld and/or portable portion of the continuous monitoring system. In particular, the receiver may comprise one or more of a customized remote control or a smartphone. However, independent of their particular embodiments, the electronics unit and/or the receiver are configured to perform the method steps as described elsewhere in this document. Herein, at least one of the electronics unit and the receiver may be operably connected to the biosensor, wherein term "operably connected" may refer to a state in which two or more objects are connected to each other in a fashion that they can interact with each other. For example, the biosensor may be operably connected to the electronics unit and/or to the receiver in a manner that the sensor signals of the biosensor may be transmitted to the electronics unit and/or to the receiver, respectively. As used herein, the term "operably connected" may also include an electrically conductive connection, wherein the biosensor may be electrically connected via at least one of a conductive adhesive material or a plug connection.

Further disclosed and proposed is a computer program including computer-executable instructions for performing one or more of the methods according to the present disclosure in one or more of the embodiments enclosed herein when the program is executed on a computer or computer network. Specifically, the computer program may be stored on a computer-readable data carrier. Thus, one, more than one, or even all of the method steps as indicated above may be performed by using a computer or a computer network, preferably by using a computer program.

Further disclosed and proposed is a computer program product having program code means, in order to perform the method according to the present disclosure in one or more of the embodiments enclosed herein when the program is executed on a computer, a computer-assisted system, or computer network. For example, the program code means may be stored on a computer-readable data carrier.

Further, the present application discloses and proposes a data carrier having a data structure stored thereon, which, after loading into a computer, a computer-assisted system, or computer network, such as into a working memory or main memory of the computer, the computer-assisted system or computer network may execute the method according to one or more of the embodiments disclosed herein.

The present application further proposes and discloses a computer program product with program code means stored on a machine-readable carrier, in order to perform the method according to one or more of the embodiments disclosed herein, when the program is executed on a computer, a computer-assisted system, or computer network. As used herein, the term "computer program product" refers to the program as a tradable product. The product may generally exist in an arbitrary format, such as in a paper format, or on a computer-readable data carrier. For example, the computer program product may be distributed over a data network, such as the internet.

The present application further proposes and discloses a modulated data signal which contains instructions readable by a computer system, a computer-assisted system, or computer network, for performing the method according to one or more of the embodiments as disclosed herein.

Preferably, referring to the computer-implemented aspects of the disclosure, one or more of the method steps or even all of the method steps of the method according to one or more of the embodiments disclosed herein may be performed by using a computer, a computer-assisted system, or computer network. Thus, generally, any of the method steps including provision and/or manipulation of data may be performed by using a computer, a computer-assisted system, or a computer network. Generally, these method steps may include any of the method steps, typically except for method steps requiring manual work, such as providing the samples and/or certain aspects of performing the actual measurements.

In a preferred embodiment, a remote control may, thus, be used as the portable device, wherein the computer program may be pre-installed and/or updated on the remote control. As used herein, the term "remote control" may refer to a portable device of the continuous monitoring system which may be configured for wirelessly operating the continuous monitoring system from a distance, particularly from a short distance, such as a few meters. The remote control may operate by using digitally-coded pulses of infrared radiation in order to control a plurality of functions of the continuous monitoring system. For this purpose, the remote control may be a wireless handheld portable device comprising an array of buttons for adjusting the functions and communicating adjustments to the continuous monitoring system. The remote control may also use both the at least one analyte value and the corresponding associated signal quality degree for further data processing, e.g., for determining the amount of insulin to be provided to the patient such as by implementing a CGM augmented bolus, i.e., a dose whose value may be better adjusted to the actual requirements of the patient due to the continuous monitoring of the analyte value in connection with the associated signal quality degrees. Further, the remote control may comprise a display on which data as received from the continuous monitoring system may be displayed, in particular one or more measured analyte values, the associated signal quality degrees, the beneficial calibration interval, and or other data which may or may not be related with the mentioned data. However, other arrangements may be feasible, such as ultrasonic radiation, motion sensor-enabled capabilities, voice control, and/or Bluetooth connectivity.

Thus, the remote control may be configured for communicating with any or all components of the continuous monitoring system. In a particularly preferred embodiment, however, the remote control may be configured for communicating only with a predetermined set of the components of the continuous monitoring system. This kind of arrangement may, in particular, allow activating access for the user only to the predetermined functions of the continuous monitoring system whereas other functions may be separately controllable.

In a preferred embodiment, a smartphone may be used as the portable device. As generally used, the term "smartphone" refers to a portable device for mobile or handheld use, usually comprising a mobile phone and a mobile operating system which may open the opportunity for using features as known from a personal computer operating system. Generally, the smartphone is equipped with a touchscreen for user interaction, is configured for running computer programs which are usually referred to as applications, abbreviated as "apps," and is adapted for internet access. Further, the smartphone may have one or more of a camera, a video camera, a voice recorder, speech recognition, near field communication, or an infrared blaster. As a result, the computer program configured for performing one or more of the methods described herein may, thus, be downloaded from the internet in form of an application. Thus, the computer program configured for performing the instructions is available on a smartphone, wherein the computer program may be configured for embedding the smartphone into the continuous monitoring system.

Consequently, the smartphone may communicate with the continuous monitoring system via the mentioned application. For this purpose, the smartphone may not only allow displaying data as received from the continuous monitoring system, adjusting the functions of the continuous monitoring system, and communicating the adjustments to the continuous monitoring system in a similar fashion as the remote control but also performing any or all of the method steps as described elsewhere in this document by using the application. However, further opportunities may also be feasible, such as displaying the data received from the continuous monitoring system by a voice output, and adjusting the functions of the continuous monitoring system via a microphone and voice recognition. Further, devices which may be denoted by the terms "personal digital assistant," "tablet computer" or "tablet" and which exhibit a number of common features with the definition as provided here may also be considered as a smartphone.

The methods described herein exhibit a number of advantages with respect to the prior art. The methods and devices disclosed herein are capable of consecutively acquiring data and deriving desired information therefrom, preferably in a nearly real, real time, or quasi-continuous approach, for frequently providing and/or updating the measured analyte values, in particular without user interaction. Consequently, the signal quality degree which is associated with a measured glucose value as determined by using the methods and devices described herein and, in particular, provided together with the associated measured glucose value to a user can, preferably, be used in a therapeutic decision and/or for a calibration in a more reliable manner compared to known continuous monitoring systems. Further, the present methods may, based on these considerations, additionally be used for monitoring a failsafe operation of the biosensor. Thus, the signal quality degree as determined here may allow providing an improved accuracy value for use as a control input into an artificial pancreas and/or for a hypoglycemic alert generation throughout the lifetime of the biosensor. Further, the calibration and, hence, the accuracy of the continuous monitoring system may also be enhanced.

Summarizing, the following embodiments are potential embodiments of the present invention. Other embodiments, however, are also feasible.

Embodiment 1

A method for providing a signal quality degree associated with an analyte value measured in a continuous monitoring system, the method comprising the steps of:
  a) receiving a measured analyte value from a biosensor, wherein the biosensor is adapted for measuring the analyte values, and wherein the biosensor is comprised in a continuous monitoring system or controlled by the continuous monitoring system;
  b) determining at least two impact parameters, wherein each of the impact parameters is influenced by an operational status of the continuous monitoring system, and wherein each of the impact parameters is capable of exerting an influence on a signal quality of the biosensor, wherein the influence of each of the impact parameters on the signal quality of the biosensor is expressed by a weight being assigned to each of the impact parameters; and
  c) determining the signal quality degree associated with the measured analyte value by combining the weights and the corresponding impact parameters; and providing the signal quality degree associated with the analyte value.

Embodiment 2

The method according to the preceding Embodiment, wherein the method is a computer-implemented method.

Embodiment 3

The method according to any one of the preceding Embodiments, wherein any or all of the method steps are performed by using a processing module.

Embodiment 4

The method according to the preceding Embodiment, wherein the processing module is one or more of:
  comprised in the continuous monitoring system;
  controlled by the continuous monitoring system;
  controlling the continuous monitoring system;
  communicating with the continuous monitoring system.

Embodiment 5

The method according to the preceding Embodiment, wherein the processing module is comprised in an electronics unit of the continuous monitoring system.

Embodiment 6

The method according to any one of the preceding Embodiments, wherein both the measured analyte value and the associated signal quality degree are, simultaneously or consecutively, communicated to a user.

Embodiment 7

The method according to any one of the preceding Embodiments, wherein the biosensor is an implantable sensor or a partially implantable sensor being indicative of the analyte glucose.

Embodiment 8

The method according to any one of the preceding Embodiments, further comprising the step of implanting the biosensor being indicative of the analyte glucose into the skin of a user.

Embodiment 9

The method according to any one of the preceding Embodiments, wherein the analyte value is measured by the biosensor in an interstitial fluid.

Embodiment 10

The method according to the preceding Embodiment, wherein the interstitial fluid comprises blood of a user.

Embodiment 11

The method according to any one of the preceding Embodiments, wherein the analyte value is measured by the biosensor subcutaneously and/or in vivo.

Embodiment 12

The method according to any one of the preceding Embodiments, wherein the analyte value is measured without user interaction.

Embodiment 13

The method according to any one of the preceding Embodiments, wherein a plurality of analyte values is measured by the biosensor.

Embodiment 14

The method according to the preceding Embodiment, wherein the plurality of the analyte values is measured within one or more of:
a fixed time interval;
a variable time interval;
at an occurrence of at least one prespecified event.

Embodiment 15

The method according to any one of the preceding Embodiments, wherein the weight is assigned to the impact parameter by a retrospective analysis of selected measured analyte values from the biosensor.

Embodiment 16

The method according to any one of the preceding Embodiments, wherein the weight is assigned to each of the impact parameters by using a multivariate function.

Embodiment 17

The method according to the preceding Embodiment, wherein the signal quality degree Q is determined by using the multivariate function $$Q = \Sigma^n_i w_i \cdot p_i, \quad (1)$$

wherein $w_i$ denotes the weight assigned to the impact parameter $p_i$, and wherein i=1 to n, wherein n denotes a number of the selected impact parameters.

Embodiment 18

The method according to any one of the preceding Embodiments, wherein the at least two impact parameters which are influenced by the operational status of the continuous monitoring system are selected from:
at least one parameter related to a Kalman filter;
a current wear time;
a current age of the biosensor;
a current concentration range;
a deviation from a mean analyte value;
a current rate of change;
at least one quantity related to a calibration of the biosensor;
a current failure probability;
a current potential of a counter electrode;
at least one process parameter of the biosensor production
a sensitivity of the biosensor; and
at least one impedance value of the biosensor.

Embodiment 19

The method according to the preceding Embodiment, wherein the at least two impact parameters (136) are selected from:
the (1,1) element of a covariance matrix of the Kalman filter;
the current rate of change;
the current potential of a counter electrode;
the current wear time of the biosensor;
a time passed since the last calibration of the biosensor; and
a sensitivity and/or an admittance of the biosensor.

Embodiment 20

The method according to any one of the two preceding Embodiments, wherein the current wear time is determined by a time interval after an electric circuit comprising the biosensor is completed.

Embodiment 21

The method according to any one of three the preceding Embodiments, wherein the current age of the biosensor is determined by a duration after a completion of the biosensor.

Embodiment 22

The method according to any one of the four preceding Embodiments, wherein the deviation from the mean analyte value is determined by comparing the measured analyte value with a mean value derived from a number of previously measured analyte values.

Embodiment 23

The method according to any one of the five preceding Embodiments, wherein the current concentration range is determined by a concentration of the analyte in the interstitial fluid of the user.

Embodiment 24

The method according to any one of the six preceding Embodiments, wherein the current rate of change is determined by recording a temporal alteration of the measured analyte value.

Embodiment 25

The method according to any one of the seven preceding Embodiments, wherein the number of valid calibrations is determined.

Embodiment 26

The method according to any one of the eight preceding Embodiments, wherein the current failure probability is determined from a probability of a failure of the biosensor.

Embodiment 27

The method according to any one of the nine preceding Embodiments, wherein the biosensor comprises an electrochemical cell having at least one working electrode and a counter electrode, wherein a predefined electrical potential is applied between the working electrode and the counter electrode.

Embodiment 28

The method according to the preceding Embodiment, wherein the electrochemical cell further has at least one reference electrode, wherein the electrical potential of the working electrode is kept constant with respect to the reference electrode by using the potentiostat and wherein the counter electrode provides for a current compensation at the working electrode.

Embodiment 29

The method according to any one of the two preceding Embodiments, wherein a sensitivity S of the biosensor or a value related thereto is determined by measuring a raw current through the working electrode of the biosensor, whereby a concentration c of the analyte is taken into account.

Embodiment 30

The method according to any one of the three preceding Embodiments, wherein a complex admittance Y of the biosensor or a value related thereto is determined by using an AC circuit.

Embodiment 31

The method according to any one of the two preceding Embodiments, wherein a relationship between the sensitivity S and the admittance Y of the biosensor, i.e., a sensitivity-to-admittance relation, is determined, wherein the sensitivity-to-admittance relation I used to acquire information about a current state of intrinsic transport properties of the membrane of the biosensor, disregarding geometric properties of the membrane.

Embodiment 32

The method according to any one of the three preceding Embodiments, wherein the impact parameter may further be selected from: an electrical capacitance C of the surface of the biosensor, an electrical resistance $R_M$ of the membrane, or a time constant $\tau = R_M \cdot C$.

Embodiment 33

The method according to any one of the preceding Embodiments, wherein the signal quality degree associated with the measured analyte value is a numerical value selected from a predefined numerical range.

Embodiment 34

The method according to any one of the preceding Embodiments, wherein the signal quality is set to a zero value within an initialization procedure.

Embodiment 35

A method for determining an amount of insulin to be delivered, the method comprising the steps of:
d) determining a signal quality degree by applying a method according to any one of the preceding Embodiments; and
e) determining the amount of insulin from at least one data pair, wherein the data pair comprises the measured analyte value from the biosensor and the signal quality degree associated with the measured analyte value.

Embodiment 36

The method according to the preceding Embodiment, wherein the data pair is communicated to a user.

Embodiment 37

A method for calibrating a continuous monitoring system, wherein at least one calibration factor is determined by comparing at least one measured analyte value with a value for an analyte content, wherein a signal quality degree associated with the measured analyte value is determined by applying the method for providing a signal quality degree associated with an analyte value measured in a continuous monitoring system, wherein the at least one measured analyte value is weighted pursuant to its associated signal quality degree.

Embodiment 38

The method according to the preceding Embodiment, wherein the at least one measured analyte value is only used for calibrating in a case in which its associated signal quality degree exceeds a predefined quality threshold.

Embodiment 39

The method according to any one of the two preceding Embodiments, wherein at least two measured analytes value are combined with respect to their associated signal quality degrees.

Embodiment 40

The method according to the preceding Embodiment, wherein a mean value of the at least two measured analyte values is formed by weighting each of the measured analyte values with a value based on the associated signal quality degree for each of the measured analyte values.

Embodiment 41

The method according to the preceding Embodiment, wherein a median of the at least two measured analyte values is formed by weighting each of the measured analyte values with a value based on the associated signal quality degree for each of the measured analyte values.

Embodiment 42

The method according to any one of the five preceding Embodiments, wherein a beneficial calibration interval is determined by applying the signal quality degrees, wherein the beneficial calibration interval is communicated to a user.

Embodiment 43

The method according to any one of the six preceding Embodiments, wherein, in an event in which the signal quality degree falls below a predefined quality threshold, an alarm is suppressed and activated after the signal quality degree meets a second predefined quality threshold.

Embodiment 44

The method according to any one of the seven preceding Embodiments, wherein, in an event in which the signal quality degree falls below a predefined quality threshold, an alarm is antedated.

Embodiment 45

A computer program product comprising executable instructions for performing a method according to any one of the preceding Embodiments referring to a method.

Embodiment 46

The computer program product according to the preceding Embodiment, wherein a computer program configured for performing the instructions is available on a portable device.

Embodiment 47

The computer program product according to the preceding Embodiment, wherein the portable device is smartphone or a remote control.

Embodiment 48

The computer program product according to the preceding Embodiment, wherein the computer program is configured for embedding the smartphone into the continuous monitoring system.

Embodiment 49

A sensor unit, comprising a biosensor, an electronics unit, and a mountable patch, wherein the electronics unit is configured for performing at least one of the methods according to any one of the preceding Embodiments referring to a method.

Embodiment 50

A continuous monitoring system, comprising a sensor unit and a receiver, wherein the sensor unit comprises a biosensor, an electronics unit, and a mountable patch, and wherein the electronics unit and/or the receiver is configured for performing at least one of the methods according to any one of the preceding Embodiments referring to a method.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
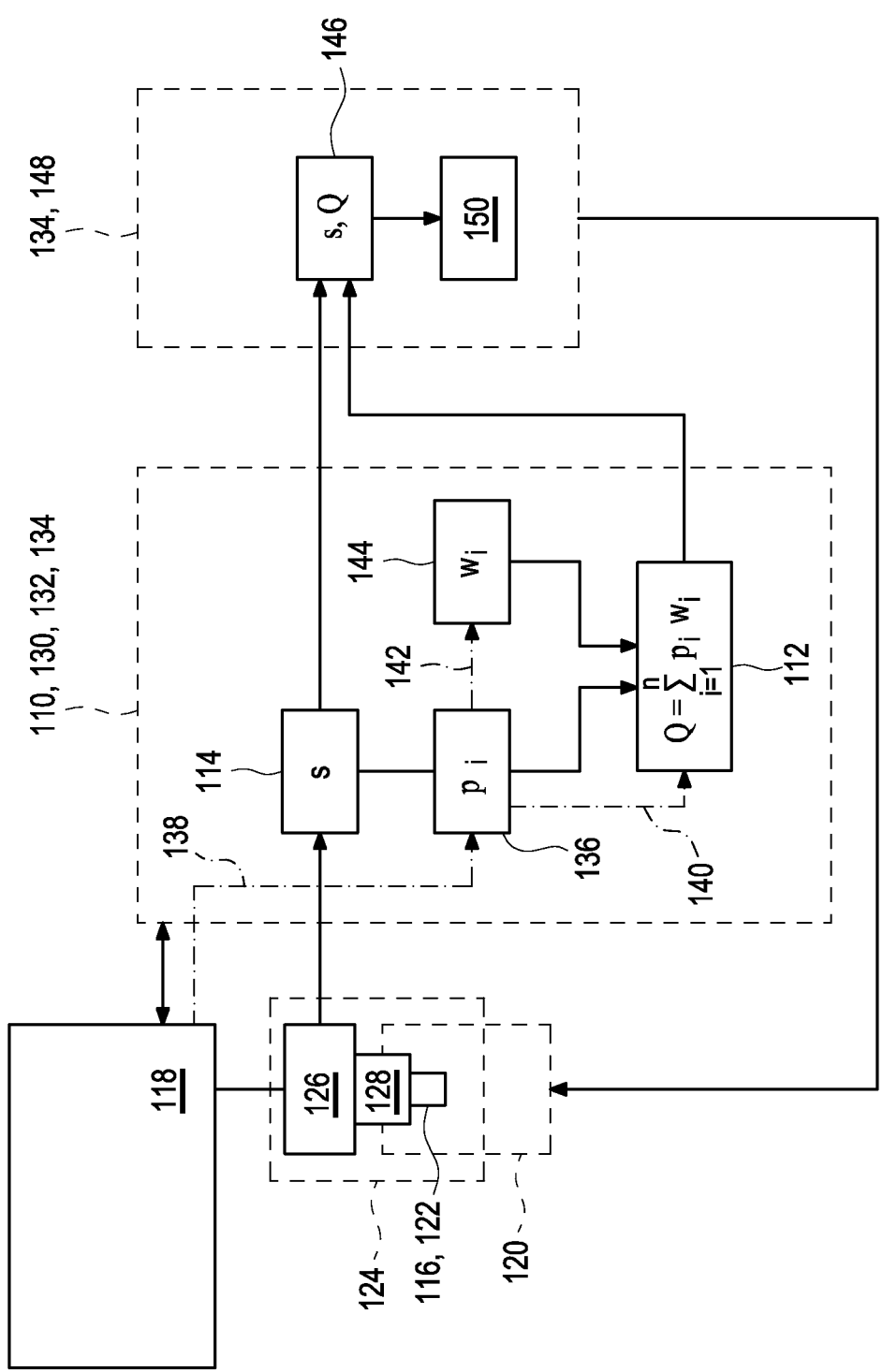
FIG. 1 schematically illustrates courses of a method for providing a signal quality degree associated with an analyte value measured in a continuous monitoring system and of a related method for determining an amount of insulin to be delivered.

FIG. 1 schematically illustrates a particularly preferred embodiment for a course of a method 110 for providing a signal quality degree 112 associated with an analyte value 114 measured in a biosensor 116, wherein the biosensor 116 is comprised in a continuous monitoring system 118 or wherein the biosensor 116 is controlled by the continuous monitoring system 118. Irrespective of details of a relationship between the biosensor 116 and the continuous monitoring system 118, the biosensor 116 is adapted for measuring the analyte values of a user 120.

In this a particularly preferred embodiment, the biosensor 116 is a fully implantable biosensor which is adapted for performing the detection of the analyte in the body fluid in a subcutaneous tissue, in particular, in an interstitial fluid. Accordingly, the implantable or transcutaneous biosensor 116 is adapted to be fully arranged within the body tissue of the user 120. For this purpose, the biosensor comprises an insertable portion 122 configured to be insertable into the body tissue. Preferably, the biosensor may fully or partially comprise a biocompatible surface, i.e., a surface which may have as little detrimental effects on the user 120 or the body tissue as possible, at least during typical durations of use. As an example, the biosensor 116, specifically the insertable portion 122 thereof, is fully or partially be covered with at least one biocompatible membrane, such as a polymer membrane or a gel membrane which, on one hand, is permeable for the body fluid, at least for the analyte comprised therein, and which, on the other hand, is adapted to retain sensor substances, such as one or more test chemicals within the sensor, thus preventing a migration thereof into the body tissue.

In this embodiment, the biosensor 116 is a part of a sensor unit 124 which, apart from the biosensor 116, comprises an electronics unit 126 and a mountable patch 128. Herein, the electronics unit 126 is adapted for performing the methods described herein, in particular, the method 110 for determining the signal quality degree 112 of the analyte value 114 measured in a continuous monitoring system 118. As schematically illustrated in FIG. 1, the mountable patch 128 is arranged on the skin of the user 120 and exhibits a connected state in which both the biosensor 116 and the electronics unit 126 are connected via the mountable patch 128 in a manner that the sensor unit 124 is operable.

In accordance with step a) of the method 110 for determining the signal quality degree 112 of the analyte value 114 measured in the biosensor 116, the analyte value 114 as measured in a biosensor 116, also denoted as s, is received by a processing module 130, wherein the processing module 130 communicates with the continuous monitoring system 118. Preferably, a computer program 132, also denominated as an application or app, configured for performing the instructions of the method 110 is available on a smartphone 134, wherein the computer program 132 is configured in this embodiment for embedding the smartphone 134 into the continuous monitoring system 118. Consequently, the smartphone 134 communicates with the continuous monitoring system 134 via the computer program 132 without interaction of the user 120.

In accordance with step b) of the method 110 for determining the signal quality degree 112 of the analyte value 114 measured in the biosensor 116, at least two impact parameters 136, also denoted by $p_1$, are determined. An operational status of the continuous monitoring system 118 exerts an influence 138 on the impact parameters 136, wherein each of the impact parameters is capable of exerting an influence 140 on the signal quality of the biosensor 116. An influence 142 of each of the impact parameters 136 on the signal quality of the biosensor 116 is expressed by a weight 144, also denoted by $w_i$, wherein the weight $w_i$ 144 is assigned to the impact parameter $p_i$ 136.

In accordance with step c) of the method 110 for providing the signal quality degree 112 to the analyte value 114 as measured in the biosensor 116, the signal quality degree 112, also denoted by Q and being associated with the measured analyte value s 114, is determined by combining the weight $w_i$ 144 being assigned to each of the impact parameter $p_i$ 136, and the corresponding impact parameter $p_i$ 136, in particular by using the multivariate function according to Equation (1):

$$Q = \Sigma^n_i w_i p_i,  \quad (1)$$

wherein $w_i$ denotes the i-th weight 144 assigned to the i-th impact parameter $p_i$ 136, wherein the serial number i is a non-negative ascending natural number within a closed interval from 1 to n, wherein n denotes the number of the selected impact parameters 136. In this fashion it can be ensured that the individual weight $w_i$ 144 is assigned to each of the n impact parameters $p_i$ 136.

The signal quality degree Q 112 as determined here may, subsequently, be provided together with the analyte value s 114a whereby it may be communicated to the user 120. However, it may be advantageous to, consecutively or, preferably, simultaneously, communicate both the measured analyte value s 114 and the corresponding signal quality degree Q 112 as a data pair 146 to the user 120. For this purpose, the course of a related method 148 for determining an amount of insulin 150 to be delivered to the user 120 is further schematically illustrated in FIG. 1. Thus, in accordance with step e) of the method 148 for determining an amount of insulin 150 to be delivered, the amount of insulin 150 may also be determined from the data pair 146.

As generally known, the measured analyte values 114 as provided by each continuous monitoring system 118, may comprise a measurement error 152, wherein the measurement error 152 is defined here by using a relative standard deviation 154 between the measured analyte values 114 and corresponding reference analyte values as a metric. However, as mentioned above, other kinds of metrics may also be applicable. A typical example in which a number 156 of observable measurement errors 152 is depicted versus the measurement error 152, which is expressed as a relative standard deviation (SRD) 154, is shown in FIG. 2.

The signal quality degree 112 associated with the measured analyte value 114 may at least partially be determined by using additional information in the form of at least two impact parameters 136, wherein each of the impact parameters 136 is influenced by the operational status of the continuous monitoring system 118. Since the signal quality degree 112 may, as mentioned above, be reciprocally related to the measurement error 152 in a manner that no expected measurement error 152 may be expressed as a high signal quality degree 112 while a large expected measurement error 152 may be expressed as a low signal quality degree 112, the number 156 of observable measurement errors 152 as, for example, depicted in FIG. 2 may be used for determining the signal quality degree 112 of the analyte value 114 measured in the continuous monitoring system 118.

Figure 2:
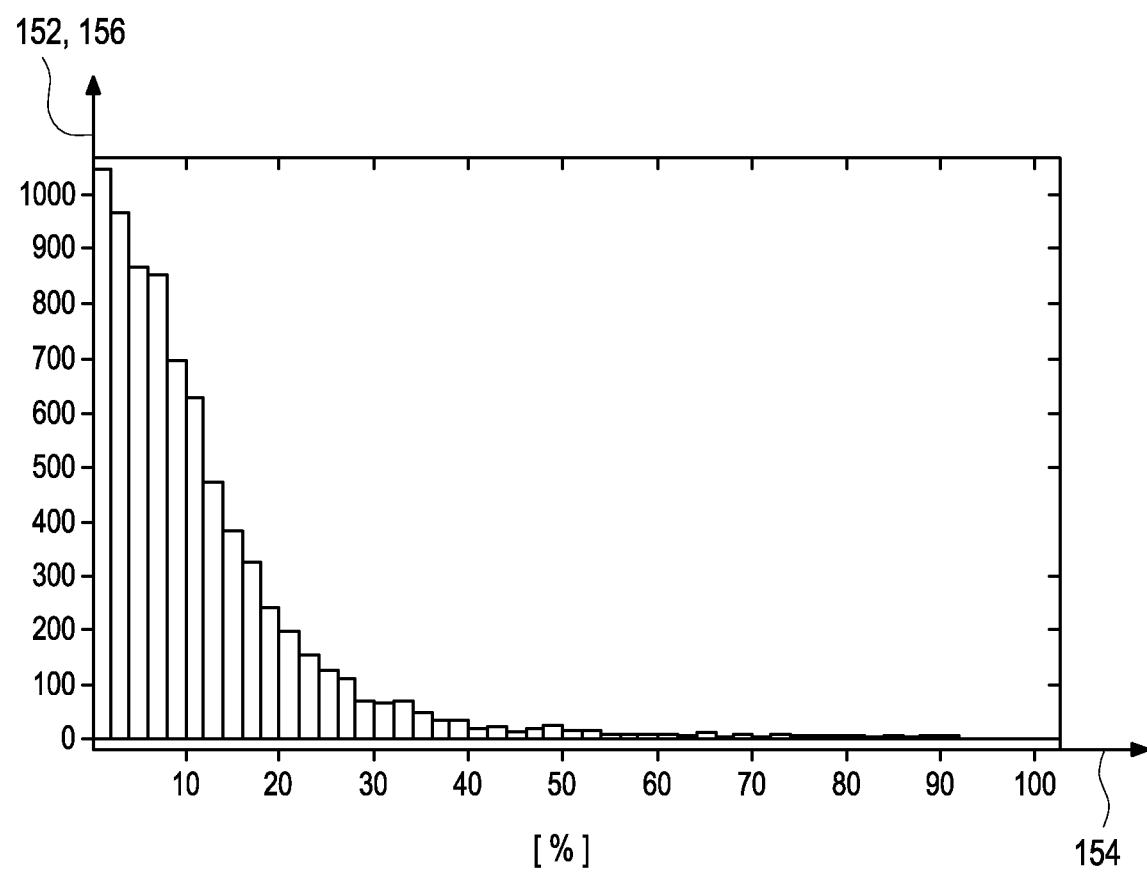
FIG. 2 illustrates a number of observable measurement errors which are depicted versus the measurement error expressed as a relative standard deviation (SRD).

Thus, the number 156 of the measurement errors 152 as illustrated in FIG. 2 can be correlated to a number of selected impact parameters 136 that may be influenced by the operational status of the continuous monitoring system 118. In the particular example shown in FIG. 2, the following five impact parameters $136_p$, i=1 to 5, have been taken into account:

| impact parameter $p_i$ | operational status of the continuous monitoring system |
|---|---|
| $p_1$ | covariance matrix of a Kalman filter |
| $p_2$ | current rate of change |
| $p_3$ | current potential of a counter electrode |
| $p_4$ | current wear time |
| $p_5$ | time passed since last calibration of continuous monitoring system |

Thus, in order to be able to predict the expected measurement errors 152, a linear model which uses the additional information to calculate the measurement error 152, has been fitted to the data as shown in FIG. 2. In this particular example, the linear model employs the Equation (2) for determining the relative standard deviation (SRD):

$$SRD = \sqrt{\left(\frac{G(t) - R(t)}{R(t)}\right)^2} = \sum_i w_i \cdot p_i + c_0 + \varepsilon \quad (2)$$

wherein G(t) denotes the measured analyte (glucose) value 114 at the time t, R(t) a reference analyte value at the same time t, $p_i$ the corresponding impact parameter, $w_i$ the corresponding coefficient indicative of the weight of the respective impact parameter $p_i$, and $\varepsilon$ the remaining unexplained error, wherein the serial number i is a non-negative ascending natural number within a closed interval from 1 to n, wherein n denotes the number of the selected kinds of additional information. Thus, Equation (2) which may be used to determine the signal quality degree Q by using the impact parameter $p_i$, and the corresponding weight $w_i$.

As mentioned above, the impact parameters 136 may, in this embodiment, be selected in the following manner. A first impact parameter $p_1$ could be derived from the (1,1) element of a covariance matrix of a Kalman filter according to Equation (3):

$$p_1 = \sqrt{P_{11}}/I \quad (3)$$

wherein $P_{11}$ denotes the (1,1) element of the covariance matrix of the Kalman filter and wherein I denotes a current value in nA as derived from the filter.

Further, a second impact parameter $p_2$ could be derived from the current rate of change according to Equation (4):

$$p_2 = |dG/dt| \quad (4)$$

wherein dG/dt denotes a current rate of change of the measured analyte (glucose) value 114 G(t) at the time t.

Further, a third impact parameter $p_3$ could be derived from a current potential of a counter electrode according to Equation (5):

$$p_3 = \begin{cases} \text{low} & U_{CE} < 850 \\ \text{normal} & 850 \leq U_{CE} \leq 1050 \\ \text{high} & U_{CE} > 1050 \end{cases} \quad (5)$$

wherein $U_{CE}$ denotes the current voltage at the counter electrode.

Further, a forth impact parameter $p_4$ could be derived from a current wear time of the biosensor 116 according to Equation (6):

$$p_4 = \begin{cases} \text{Early phase} & \text{Sensor Use Time} < 3 \text{ days} \\ \text{Late phase} & \text{Sensor Use Time} \geq 3 \text{ days} \end{cases} \quad (6)$$

wherein the Sensor Use Time denotes the time of wear of the biosensor 116 as described above in more detail.

Further, a fifth impact parameter $p_5$ could be derived from a time passed since the last calibration of the biosensor 116 according to Equation (7):

$$p_5 = t_{calibration} \quad (7)$$

wherein $t_{calibration}$ denotes a time in minutes which has passed since the last calibration of the biosensor 116.

Thus, in the embodiment as illustrated in FIG. 2, five different kinds of impact factors $p_i$, i=1 to 5, have been considered. However, in alternative embodiments, a further and/or another impact parameter may, alternatively or in addition, be taken into account.

Applying this kind of linear model to a set of clinical data as recorded by the corresponding continuous monitoring system 118, the following results for estimating the relative standard deviation (SRD) as illustrated in FIG. 2 have been obtained:

| weight $w_i$ | estimated value | standard error |
|---|---|---|
| $w_0$ | 18.661 | 3.1806 |
| $w_1$ | 23.172 | 0.91556 |
| $w_2$ | 1.9827 | 0.17837 |
| $w_{3\_low}$ | Baseline | — |
| $w_{3\_normal}$ | −10.981 | 3.1671 |
| $w_{3\_high}$ | −9.9054 | 3.1753 |
| $w_{4\_late\ phase}$ | −4.0178 | 0.24495 |
| $w_{4\_early\ phase}$ | Baseline | — |
| $w_5$ | 0.001518 | 0.00053343 |

Estimating the weights $w_i$ for this kind of model may be applied for providing an estimation about the typical measurement error 152 of a certain measured analyte value 114 by using the following impact factors $p_i$, i=1 to 5:

| | |
|---|---|
| $p_1$ | 0.12; |
| $p_2$ | 1.1 mg/dl/min |
| $p_3$ | normal |
| $p_4$ | early phase |
| $p_5$ | 800 minutes |

As a result, the relative standard deviation (SRD) may be determined according to Equation (8):

$$SRD = \sum_i^n w_i \cdot p_i = 18.661 + 23.172 \cdot 0.12 + 1.9827 \cdot 1.1 - 10.981 + 0 + 0.001518 \cdot 800 = 13.85 \quad (8)$$

In a particular embodiment, 100% sensor quality degree may be defined as a relative standard deviation of 5 or less while 0% sensor quality degree may be defined as a relative standard deviation of 25 or more, any value of the relative standard deviation may be related to the sensor quality degree. In this particular example, the sensor quality degree can be determined according to Equation (9):

$$Q = 13.85 \cdot 100\%/(25-5) = 69.25\% \quad (9)$$

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS

110 method for providing a signal quality degree associated with an analyte value
112 signal quality degree Q
114 measured analyte value s
116 biosensor
118 continuous monitoring system
120 user
122 implantable biosensor
124 sensor unit
126 electronics unit
128 mountable patch
130 processing module
132 computer program
134 smartphone
136 impact parameters $p_i$
138 influence
140 influence
142 influence
144 weight $w_i$
146 data pair
148 method for determining an amount of insulin
150 amount of insulin
152 measurement error
154 relative absolute standard deviation
156 number of observable measurement errors

What is claimed is:

1. A method for calibrating a continuous monitoring system, wherein at least one calibration factor is determined by comparing at least one measured analyte value with a value for an analyte content, wherein a signal quality degree associated with the measured analyte value is determined by applying a method for providing a signal quality degree associated with an analyte value measured in a continuous monitoring system, and wherein the at least one measured analyte value is weighted pursuant to its associated signal quality degree;
  wherein the signal quality degree associated with the measured analyte value is determined and applied by the following steps:
  a) receiving a measured analyte value from a biosensor, wherein the biosensor is adapted for measuring the analyte values, and wherein the biosensor is included in the continuous monitoring system or controlled by the continuous monitoring system;
  b) determining at least two impact parameters, wherein each of the impact parameters is influenced by an operational status of the continuous monitoring system, and wherein each of the impact parameters is capable of exerting an influence on a signal quality of the biosensor, wherein the influence of each of the impact parameters on the signal quality of the biosensor is expressed by a weight assigned to each of the impact parameters;

c) determining the signal quality degree associated with the measured analyte value as a function of the weights and the corresponding impact parameters; and providing the signal quality degree associated with the analyte value; and d) wherein at least two measured analyte values are combined as a function of the associated signal quality degrees of the at least two measured analyte values when determining the at least one calibration factor.

2. The method for calibrating of claim 1 wherein the at least two measured analyte values are combined using one of the following steps:

a) wherein a mean value of the at least two measured analyte values is determined by weighting each of the at least two measured analyte values with a value based on the associated signal quality degree for each of the measured analyte values; and b) wherein a median of the at least two measured analyte values is determined by weighting each of the at least two measured analyte values with a value based on the associated signal quality degree for each of the measured analyte values.

3. The method of claim 1, wherein the biosensor is an implantable sensor or a partially implantable sensor being indicative of the analyte glucose, wherein the analyte value is measured by the biosensor in an interstitial fluid subcutaneously, and wherein the analyte value is measured without interaction of a user.

4. The method of claim 3, wherein the analyte value is measured by the biosensor in vivo.

5. The method of claim 1, wherein the weight is assigned to the impact parameter by a retrospective analysis of selected measured analyte values from the biosensor and wherein the weight is assigned to each of the impact parameters by using a multivariate function.

6. The method of claim 5, wherein the signal quality degree Q is determined by using the multivariate function:

$$Q = \Sigma n i w i \cdot p i, \quad (1)$$

wherein wi denotes the weight assigned to the impact parameter pi, and wherein i=1, n, wherein n denotes a number of the impact parameters.

7. The method of claim 1, wherein the at least two impact parameters which are influenced by the operational status of the continuous monitoring system are selected from:
at least one parameter related to a Kalman filter;
a current wear time of the biosensor;
a current age of the biosensor;
a current concentration range;
a deviation from a mean analyte value;
a current rate of change;
at least one quantity related to a calibration of the biosensor;
a current failure probability;
a current potential of a counter electrode;
at least one process parameter of the production of the biosensor;
a sensitivity of the biosensor; and/or
at least one impedance value of the biosensor.

8. The method of claim 7, wherein the at least two impact parameters are selected from:
the (1,1) element of a covariance matrix of the Kalman filter;
the current rate of change;
the current potential of a counter electrode;
the current wear time of the biosensor;
a time passed since the last calibration of the biosensor;
a sensitivity of the biosensor; and/or
an admittance of the biosensor.

9. The method of claim 7, wherein one of the selected impact parameters is the current wear time and wherein the current wear time is determined by a time interval after an application of the biosensor to the user.

10. The method of claim 7, wherein one of the selected impact parameters is the current age of the biosensor and wherein the current age of the biosensor is determined by a duration after a completion of the biosensor.

11. The method of claim 7, wherein one of the selected impact parameters is the current concentration range and wherein the current concentration range is determined by a concentration of the analyte in the interstitial fluid of the user.

12. The method of claim 7, wherein one of the selected impact parameters is the deviation from the mean analyte value and wherein the deviation from the mean analyte value is determined by comparing the measured analyte value with a mean value derived from a number of previously measured analyte values.

13. The method of claim 7, wherein one of the selected impact parameters is the current rate of change and wherein the current rate of change is determined by a recording a temporal alteration of the measured analyte value.

14. The method of claim 7, wherein one of the selected impact parameters is the current failure probability and wherein the current failure probability is determined from a probability of a failure of the biosensor.

15. The method of claim 7, wherein one of the selected impact parameters is the current potential of the counter electrode and wherein the biosensor comprises an electrochemical cell having at least one working electrode and the counter electrode, wherein a predefined electrical potential is applied between the working electrode and the counter electrode, wherein the current potential of the counter electrode is determined by recording a deviation from the predefined electrical potential, whereby at least one of the sensitivity and the admittance of the biosensor is measured.

16. The method of claim 1 further comprising the step of determining a calibration interval as a function of the signal quality degrees of the at least two measured analyte values used to determine the at least one calibration factor.

17. A method for calibrating a continuous monitoring system, wherein at least one calibration factor is determined by comparing at least one measured analyte value with a value for an analyte content, wherein a signal quality degree associated with the measured analyte value is determined by applying a method for providing a signal quality degree associated with an analyte value measured in a continuous monitoring system, and wherein the at least one measured analyte value is weighted pursuant to its associated signal quality degree;

wherein the signal quality degree associated with the measured analyte value is determined by the following steps:

a) receiving a measured analyte value from a biosensor, wherein the biosensor is adapted for measuring the analyte values, and wherein the biosensor is included in the continuous monitoring system or controlled by the continuous monitoring system;

b) determining at least two impact parameters, wherein each of the impact parameters is influenced by an operational status of the continuous monitoring system, and wherein each of the impact parameters is capable of exerting an influence on a signal quality of the biosensor, wherein the influence of each of the impact parameters on the signal quality of the biosensor is expressed by a weight assigned to each of the impact parameters;

c) determining the signal quality degree associated with the measured analyte value as a function of the weights and the corresponding impact parameters; and providing the signal quality degree associated with the analyte value; and wherein one of the selected impact parameters is the number of calibrations and wherein the number of calibrations is determined by counting calibration procedures previously performed with the biosensor and wherein another one of the at least two impact parameters which are influenced by the operational status of the continuous monitoring system is selected from:

at least one parameter related to a Kalman filter;
a current wear time of the biosensor;
a current age of the biosensor;
a current concentration range;
a deviation from a mean analyte value;
a current rate of change;
at least one quantity related to a calibration of the biosensor;
a current failure probability;
a current potential of a counter electrode;
at least one process parameter of the production of the biosensor;
a sensitivity of the biosensor; and/or
at least one impedance value of the biosensor.

* * * * *